(12) United States Patent
Damren

(10) Patent No.: US 10,934,515 B2
(45) Date of Patent: Mar. 2, 2021

(54) PASSIVE AUTOMATIC ANTIFOAM DELIVERY SYSTEM FOR USE WITH SINGLE-USE BIOREACTORS

(71) Applicant: GLOBAL LIFE SCIENCES SOLUTIONS USA LLC, Marlborough, MA (US)

(72) Inventor: Richard Lee Damren, Marlborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 101 days.

(21) Appl. No.: 15/749,401

(22) PCT Filed: Aug. 15, 2016

(86) PCT No.: PCT/EP2016/069334
§ 371 (c)(1),
(2) Date: Jan. 31, 2018

(87) PCT Pub. No.: WO2017/029259
PCT Pub. Date: Feb. 23, 2017

(65) Prior Publication Data
US 2018/0223240 A1    Aug. 9, 2018

Related U.S. Application Data

(63) Continuation-in-part of application No. 14/830,306, filed on Aug. 19, 2015, now abandoned.

(51) Int. Cl.
*C12M 1/21* (2006.01)
*C12M 1/00* (2006.01)

(52) U.S. Cl.
CPC ............ *C12M 41/02* (2013.01); *C12M 23/14* (2013.01); *C12M 23/28* (2013.01)

(58) Field of Classification Search
None
See application file for complete search history.

(56) References Cited

U.S. PATENT DOCUMENTS 2,981,693 A * 4/1961 Browne ................... G05D 9/12
516/115
4,987,082 A * 1/1991 Gallagher .............. C12M 41/02
307/118

(Continued)

FOREIGN PATENT DOCUMENTS

DE      8430978 U1    2/1985
DE      3850652 T2   10/1994

(Continued)

OTHER PUBLICATIONS

Thomson Scientific, London, GB; AN 2006-641618; XP002763801, & JP 2006247852A (Seiko Epson Corp); Sep. 21, 2006; Abstract.

*Primary Examiner* — Christopher P Jones
*Assistant Examiner* — Phillip Y Shao
(74) *Attorney, Agent, or Firm* — Grogan, Tuccillo & Vanderleeden, LLP

(57) ABSTRACT

The aspects of the disclosed embodiments generally relate to an apparatus which allows for the controlled addition of antifoam to the foam present in the headspace of a disposable single-use bioreactor in a reliable manner. The aspects of the disclosed embodiments also generally relate to a method of using such apparatus which allows for the controlled addition of antifoam to the foam present in the headspace of a disposable single-use bioreactor in a reliable manner. The aspects of the disclosed embodiments generally relate to antifoam systems, methods and apparatus, and more particularly, to an antifoam device operably connected to a single use biobag.

19 Claims, 7 Drawing Sheets

(56) References Cited

Figure 1:
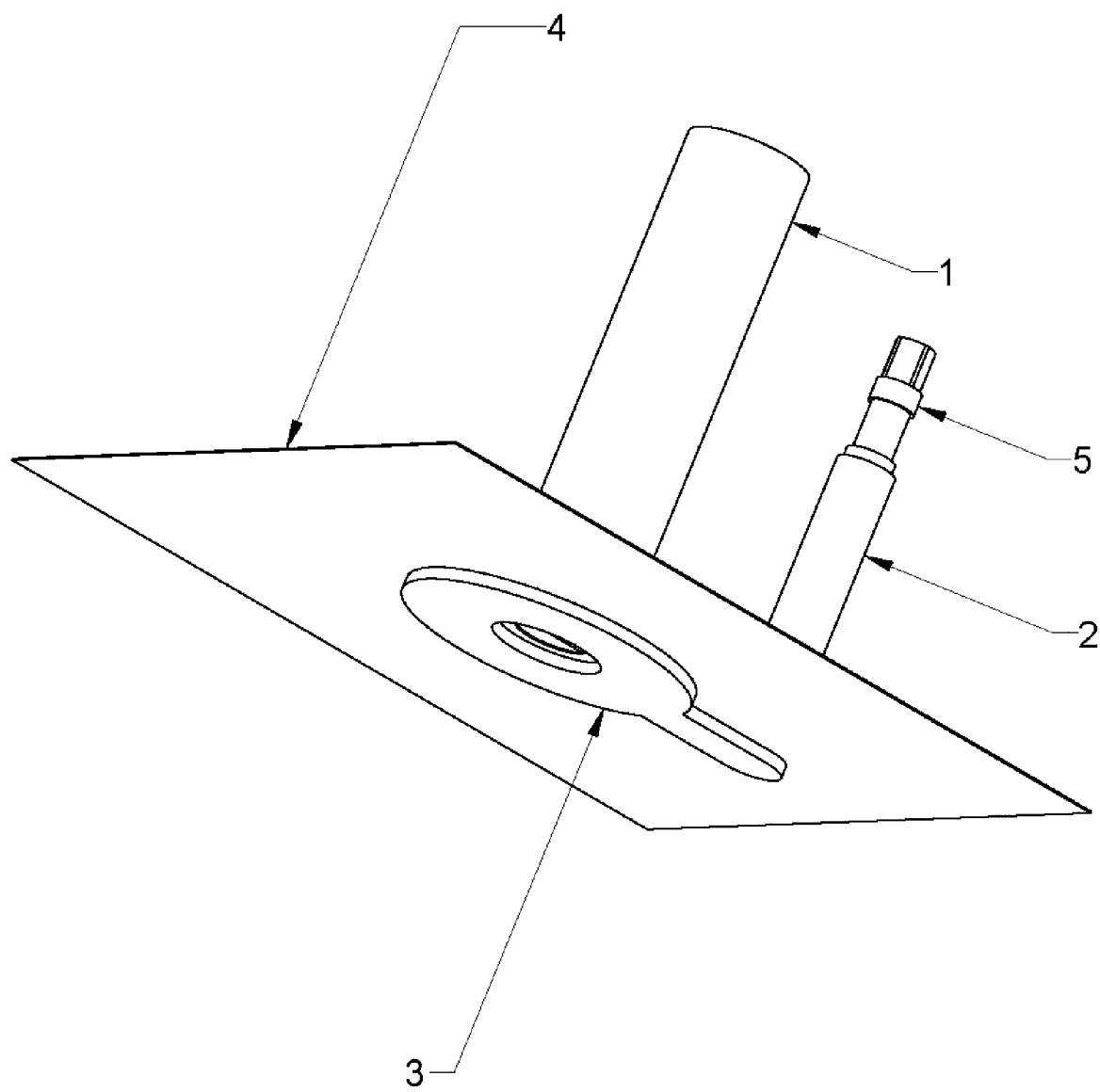

U.S. PATENT DOCUMENTS 6,465,243 B2* 10/2002 Okada .................... C12M 29/02
422/105
2015/0198549 A1* 7/2015 Kjar ....................... C12M 33/04
435/3

FOREIGN PATENT DOCUMENTS

| DE | 102013109820 A1 | 3/2015 |
| WO | 9815302 A1 | 4/1998 |
| WO | 2008088371 A2 | 7/2008 |
| WO | 2015109192 A1 | 7/2015 |

* cited by examiner

PASSIVE AUTOMATIC ANTIFOAM DELIVERY SYSTEM FOR USE WITH SINGLE-USE BIOREACTORS

CROSS-REFERENCE TO RELATED APPLICATIONS

This application is a continuation-in-part of U.S. patent application Ser. No. 14/830,306, filed Aug. 19, 2015, and a national stage of International Application No. PCT/EP2016/069334 filed Aug. 15, 2016 which is based upon and claims priority to U.S. patent application Ser. No. 14/830,306, the entire contents of all of which are incorporated herein by reference in their entireties.

FIELD

The aspects of the disclosed embodiments generally related to an apparatus which allows for the controlled addition of antifoam to the foam present in the headspace of a disposable single-use bioreactor in a reliable manner. The aspects of the disclosed embodiments generally related to also directed to a method of using such apparatus which allows for the controlled addition of antifoam to the foam present in the headspace of a disposable single-use bioreactor in a reliable manner. The aspects of the disclosed embodiments generally relate to antifoam systems, methods and apparatus, and more particularly, to an antifoam device operably connected to a single use biobag.

DISCUSSION OF ART

A bioreactor is a device or apparatus in the form of a closed chamber or vessel in which living organisms such as mammalian cells, bacteria or yeast synthesize substances useful to the pharmaceutical and biotech industries under controlled conditions favorable to that specific organism. Traditionally bioreactors were closed, rigid stainless steel vessels in which the organisms were grown. A relatively recent development has been the appearance of systems specifically designed to use disposable, single-use flexible liners or bags to provide the sterile envelope for the cells which is supported by a rigid external support structure. Single-use when used in the context of a single-use bioreactor is generally acknowledged to mean a flexible container, liner or bag incorporating all of the functional aspects required of a traditional bioreactor which can be filled with the materials required for the growth of mammalian cells, bacteria or yeast and is designed with the intention that it be disposed of at the completion of a single production run. Disposable in this instance means that the device is designed to be low cost and to incorporate materials which can be easily disposed of using commonly available waste processing infrastructure and not require special disposal requirements. The advantages of disposable single-use systems are: the elimination of the complicated production plant infrastructure piping and systems required to clean and sterilize a rigid vessel in place, the elimination of the system downtime required for the cleaning process, elimination of the materials, time and effort required to validate the sterility of the cleaned vessel, elimination the handling requirements for the caustic chemicals used in the cleaning process and the elimination of wastes that are generated as part of the traditional cleaning process. The disposable, single use liner or bag is delivered to the customer as a closed, sterilized container which can be easily disposed of when the production run has been completed. The turnaround time for a single-use bioreactor system is greatly reduced since it basically consists of the a quick sanitization of the used bag, removal of the used bag from the support structure/vessel and the installation of the new bag to be used for the next production run into the support structure/vessel. U.S. Pat. No. 7,629,167 issued Dec. 8, 2009, which is here by incorporated by reference in its entirety, describes many such bioreactors.

One of the main disadvantages of single use, disposable bioreactors is that the plastic films used to create the flexible liners or bags are not high strength materials. The plastic films need to be thin so that they are flexible enough to be easily handled during installation into the external rigid support structure. Using thin plastic films also allow the single use bioreactor to be able to be folded into a smaller size package for shipment to customers. When microorganisms are grown inside a bioreactor their metabolism generates heat which must be removed from the bioreactor to prevent it from building up to levels that can inhibit growth of the microorganisms or even result in the death of the microorganisms. The heat produced by the microorganisms inside the bioreactor must pass through the flexible bioreactor container wall in order for it to be removed from the system. Plastic materials are not good conductors of heat so the thinner the plastic film that comprises the walls of the disposable, single-use flexible bioreactor bags can be, the better the rate of heat transfer that can be achieved. For these reasons the thin plastic films used to make the flexible bioreactor bag results in a bag or container that cannot withstand high pressures. Pressures of just a few pounds per square inch can create leaks in the envelope of these bags and this compromises the integrity of the bag and renders such a compromised bag susceptible to contamination by harmful organisms in the environment external to the bag.

Growing mammalian cells, bacteria or yeast in a bioreactor also often results in the production of an unwanted foam layer which floats at the top of the liquid in the bioreactor. This foam layer is the result of several factors. Microorganisms commonly used in the production of useful pharmaceutical or biological substances are aerobic, that is they require air to survive. In a standard stirred vessel bioreactor the required pressurized air is introduced at the bottom of the vessel in the form of small air bubbles and the vessel contains one or more impellers which are used to mix or stir the air bubbles into the liquid and to break the bubbles into smaller bubbles if possible. Even though they are being agitated or mixed by the action of the impeller(s) the buoyancy of these bubbles causes them to eventually rise to the top of the liquid surface. The liquid growth media used to grow living organisms in a bioreactor contains a wide array of substances and materials which are used as basic nutrients and growth factors by each specific type of organism that might be grown in a bioreactor. Many of these materials required by the organisms to survive also promote the formation more stable bubbles and thus a more stable foam layer at the surface of the liquid than would be the case for bubbles formed in pure water. Living organisms in a bioreactor also generate waste products as part of their metabolism and some of the waste materials also contribute to the formation of stable bubbles and foam. A constant flow of pressurized air is required to be introduced into the bottom of the bioreactor and this produces the constant creation of more bubbles and foam to be added to the existing foam layer. Bubbles making up the foam layer at the top surface of the liquid will have some lifetime during which they will persist, but eventually they will burst. If the foam layer has been made more stable as described in the preceding text, then the thickness of the foam layer will increase until the rate of bubble formation and the rate of bubbles bursting reaches equilibrium. The thickness of this foam layer in the absence of any antifoam compound may become unacceptably thick. To reduce this foam layer at the top of a bioreactor to a reasonable thickness various commercially available antifoam compounds have been developed. The effectiveness of these antifoam compounds is not constant over time requiring that several applications of the antifoam compound be applied to the foam during a single production run. The rate of foam production and the effectiveness of the antifoam in reducing the form layer produced varies widely depending on the particular materials and conditions required to cultivate each different type of microorganism in a bioreactor.

There is a space at the top of the single-use bioreactor bag called a headspace which is intended to be used to as a space for some amount of this foam to exist in. The intent is for this headspace to be large enough to contain a reasonable foam layer thickness and also to be large enough to include an additional clear space above the top of the foam layer. At the top of the bioreactor bag above where the top of the foam layer is expected to end is a ported opening in the bag wall to which a tube external to the bag is connected which provides a closed pathway to an exhaust filter through which the exhaust air flow can exit the bag. The exhaust filter allows waste gasses to flow out of the bag but prevents potentially harmful organisms in the environment external to the bag from entering the inside of the bag where they could contaminate the desired population of organisms. The exhaust tubing and the exhaust filter during normal operating conditions will allow the constant flow of exhaust gasses through this pathway without creating an undesirable level of back pressure. If the foam layer at the top of the liquid in the headspace of the bag becomes thicker than the headspace can accommodate then some of the foam can be drawn into the exhaust tube and/or exhaust filter by the flow of the exiting exhaust gas. This foam can decrease the effective size of the flow path though the exhaust tubing or can be deposited on the exhaust filter porous filter material reducing its effective surface area both of which will restrict the exhaust gas flow rate out of the bioreactor bag. A restriction in the exhaust gas flow rate from the bioreactor bag will increase the back pressure in this exhaust path and thus increase the pressure within the bioreactor bag itself. Since single-use bioreactor bags are made of thin flexible sheets of plastic film they are inherently low pressure systems. A high enough back pressure in the exhaust gas pathway can increase the pressure within the bioreactor bag to levels which may compromise the integrity of the bioreactor bag.

In an effort to control the level of foam at the top surface of the liquid in a bioreactor different antifoam addition strategies have been developed. For a few cultures of microorganisms in which the materials required for growth do not promote stable foam or where required air flow rates are low a single application of a small amount of antifoam at the start of the production run may be sufficient to control foam levels. Other microorganisms may require materials in the growth media or air flow rates which require antifoam to be applied several times during a production run, possibly on some predefined schedule. Most microorganisms require materials in the growth media or air flow at rates that lead to excessive foam generation and thus call for more elaborate strategies of foam control. One of the simplest strategies of antifoam addition depends on human operators to observe foam levels during a production run and add antifoam when they determine that it is needed. This strategy is inherently subjective and may lead to the addition of too much antifoam which would need to be removed by downstream purification processes or the addition of too little antifoam which risks blocking the exhaust gas path. Depending on the requirements of the downstream purification process, after the conclusion of a production run any residual antifoam present in a culture may need to be removed from the process fluid stream during downstream processing. The antifoam itself may have minor detrimental effects on the growth rate of the microorganism during the production run. These factors cause any antifoam addition strategy to be based on adding the absolute minimum of antifoam required to reliably control the foam level.

In theory an automated system for antifoam addition would only add antifoam as needed. The basic functional blocks of such an active control system would be a sensor, a system controller, and an actuator. The overall foam control system would be connected such that there is a feedback pathway for foam level information from the foam sensor to be input to the system controller and output pathway for a control signal to be sent from the system controller to the actuator. The foam sensor measures some physical aspect of the foam and sends that information to the system controller. The system controller can take that sensor information and determine if it needs to act on that information. If the system controller determines that action is required it can send a control signal to the actuator that causes the actuator to perform some action that initiates the addition of antifoam which in turn affects the foam level in a manner that is desirable.

An antifoam control system for a single use bioreactor can be described in more detail as follows. An active control system for bioreactor foam control requires a sensor that can measure some physical aspect of foam such that it can determine if foam is present in the headspace of the bioreactor and ideally correlate this physical measurement to the amount of foam present. For example the foam sensor can be based on some physical electrical measurement such as the capacitance, resistance or conductance at some location in the bioreactor headspace. Another example of a foam sensor is based on some optical property measured at some location in the bioreactor headspace that performs the same function.

An active control system for bioreactor foam control requires a system controller that can take the measurement signal from the foam sensor and determine if it needs to act on that information. An example of a system controller for foam control could be a digital controller such as a microcontroller or a microprocessor. Another example of a system controller for foam control could be an analog controller based on an analog comparator. Another example of a system controller for foam control could be a human who takes the information from the sensor and determines if action should be taken to reduce the foam level An active control system for bioreactor foam control requires an actuator that can be controlled by the system controller to perform some action that affects the level of foam present in the bioreactor headspace as desired. An example of an actuator used in a foam control system could be a valve that allows chemical antifoam to be added to the bioreactor headspace which would reduce foam. Another example of an actuator used in a foam control system could be a pump that allows chemical antifoam to be pumped into the bioreactor headspace to reduce foam. Another example of an actuator used in a foam control system could be a mechanical agitator such as an impeller located in the bioreactor headspace which mechanically breaks up the foam. Another example of an actuator used in a foam control system could be a human who manually adds chemical antifoam to the bioreactor headspace or performs some action that reduces the level of foam as desired.

Such active foam control systems are presently available for foam control in bioreactors but are not widely used. The reliability of foam control systems at the present time is not high enough to make automated systems widely accepted. Problems inherent in such active controls systems are incorrect information from the foam sensor, inappropriate action taken by the system controller and ineffective effects by the actuator on the foam level.

Incorrect information from the foam sensor can take the form of no detection of the existing foam level (false negative), information that does not correlate to the foam level or, an incorrect indication that foam is present (false positive). These errors in detecting foam by foam sensors can arise from the difficulties inherent in detecting foam due to differences in the measurable properties of foam in different bioreactor process conditions. For example different bioreactor process conditions can generate foam with different electrical properties and different optical properties. Condensation of moist air in the headspace of a bioreactor into droplets on the foam sensor detecting element may be falsely interpreted by the sensor as being foam. Errors in detecting foam by foam sensors can also be due to problems related to that specific instance of foam sensor, i.e. that particular foam sensor has failed. The reliability of foam sensors at the present time is not high enough to make automated foam control systems widely accepted.

Since the system controller is the core of a foam control feedback system inappropriate action taken by the system controller can be due to not tailoring the system controller's control strategy to differences in bioreactor process conditions. This inappropriate action can be caused by incorrect inputs to the system controller or by incorrect levels of output by the controller to the actuator. An example would be when different bioreactor process conditions generate foam with different physical properties which affect the accuracy of the foam level reading from the foam sensor. Another example would be that different bioreactor process conditions can generate foam with different physical properties which affect the effectiveness of the system foam control method in reducing the level of that particular foam. Errors in system controller response to foam can also be due to problems related to that specific instance of system controller, i.e. that particular system controller has failed.

There is thus a great need to improve foam control in bioreactors.

BRIEF DESCRIPTION

The aspects of the disclosed embodiments generally relate to an apparatus (also called a system) which allows for controlled addition of antifoam to foam present in the headspace of a disposable single-use bioreactor in an efficient and reliable manner.

The basic configuration of the apparatus includes one or more pads or wicks made of porous or fibrous materials which are located inside the headspace of a single-use bioreactor bag in close proximity to the exhaust gas exit port(s) or in the exhaust gas tube or line. The porous or fibrous wicks or rings are operably connected to an external rigid or flexible antifoam reservoir attached to the bag through a port fitment welded into the bioreactor bag wall.

The port fitment is connected to tubing which creates an enclosed pathway between the external antifoam reservoir and the wicks or rings located internally to the bioreactor bag. Antifoam is introduced into the external antifoam reservoir by the user such as via a sterile syringe fitting or by tube welding on a small container of antifoam. The antifoam in the antifoam reservoir then flows through the enclosed pathway and is absorbed or wicked into the porous or fibrous material of the wicks or rings such as by a capillary transfer mechanism. Surface tension of the antifoam would ensure that the antifoam remained suspended in the porous or fibrous material of the wicks or rings until foam from the bioreactor rose to the level where it made contact with the antifoam soaked wicks or rings.

Once the foam in the bioreactor rises to a level where it makes contact with the wicks or rings a small amount of antifoam is transferred to the bioreactor foam mass. This automatic application of antifoam to the bioreactor foam reduces the level of the bioreactor foam in the bioreactor bag headspace. A capillary transfer mechanism (wicking) automatically replaces the antifoam in the wicks or rings that had been applied to the foam mass in the bioreactor bag. This is a self-regulating antifoam control system that requires no outside intervention to repeatedly cycle and operate as needed after the initial filling of the antifoam reservoir. This apparatus thus passively regulates the amount of antifoam applied to the bioreactor foam and applies the antifoam only as needed.

The passive system as described above would not exclude the possibility of making an antifoam application on demand as desired by the user. A force or pressure could be applied to the external antifoam reservoir in such a manner that it created an increased pressure inside the antifoam reservoir which would cause antifoam to be expelled from the wicks or rings where it would make contact with the foam layer in the bioreactor headspace.

This apparatus is passive in that it does not require a sensor to detect foam, nor an active control system to act on information from a foam sensor to apply a controlled amount of antifoam to the headspace of a disposable single-use bioreactor. This passive system also does not require a power source to operate which is in contrast to an active system. Thus this passive system does not suffer the reliability problems associated with existing active control systems for bioreactor foam control. Aspects of the disclosed embodiments also generally relate to a much needed integral control that is presently lacking in bioreactor systems.

One aspect of the exemplary embodiments is also directed to a passive automatic antifoam delivery system for use with single-use bioreactors comprising:

a porous or fibrous object, which can suitably be non-reactive and/or of medical grade, secured proximally to the exhaust port of the bioreactor (such as a cylindrical wick or a ring);

wherein said porous or fibrous material absorbs/wicks antifoam from the antifoam reservoir and retains said antifoam therein until foam from the bioreactor rises to the level wherein it makes contact with the antifoam absorbed/wicked porous or fibrous object which releases small quantities of antifoam sufficient to reduce foam below the exhaust port.

Another aspect of the exemplary embodiments is directed to an object (e.g. a cylindrical wick or a ring) of porous or fibrous material, suitably of medical grade; wherein said porous or fibrous material is absorbed/wicked with antifoam and retains it therein until exposed to a mass of foam which causes the release of small quantities of antifoam sufficient to neutralize the foam from the mass.

Another aspect of the exemplary embodiments is directed to the use of an object (e.g. a cylindrical wick or a ring) of porous or fibrous material, suitably of medical grade, to neutralize foam in a bioreactor comprising:

securing said porous or fibrous material around or adjacent to the exhaust port in the top of a single-use bioreactor bag;

absorbing/wicking antifoam onto the porous or fibrous material;

retaining antifoam absorbed/wicked porous or fibrous material therein until exposed to a mass of foam which causes the release of small quantities of antifoam sufficient to neutralize the foam from the mass.

Medical grade porous or fibrous material as used herein refers to a biocompatible material not having toxic or negative effects on the growth of organisms commonly used in the pharmaceutical industry or on the useful products produced by such organisms. Such material could be formed from open cell porous foams, fibrous mesh or pads or sintered bead foams made from a wide range of materials such as polymeric plastic materials like polyethylene, polypropylene, polyester, polyolefins, polyamides, polyurethane, acrylics, styrenics, etc. or from metals or metal alloys such as titanium or stainless steel or from ceramics such as silicon nitride, and zirconium dioxide. The material is suitably permeable to liquids and may have an open pore structure with pores e.g. in the 1-3000 μm range, such as 2-2000 μm or 50-2000 μm. Larger pores can be more suitable for viscous and/or particle-containing antifoams, while smaller pores may be preferred for low viscosity antifoams.

Anti-foaming agents are hydrophobic agents such as polydimethylsiloxane with silica (such as XIAMETER® products including Antifoam 2210 or Compound A AFE-1520 Antifoam Emulsion, AFE-1510 Antifoam Emulsion, AFE-0010 Antifoam Emulsion FG, ACP-1920 Powdered Antifoam, and AFE-0100 AF Emulsion FG (Dow Corning), M-10 (Calgene), Breox FMT 30 (Block copolymer of polyethylene glycol and polypropylene glycol having a molecular weight of approximately 3,000, available from BP Chemicals Ltd.); Darastil 8231 (Block copolymer of polyethylene glycol and polypropylene glycol having a molecular weight of approximately 2,000, available from Grace Dearborn Ltd.), Sigma-Aldrich Antifoams 204 (A6426 and A8311 containing a mixture of organic non-silicone polypropylene based polyether dispersions), A6582 (100% silicone based polymer that has a molecular weight range of 3,200 to 16,500 Da consist of particles ranging in size from 10 to 40 microns, and can be removed by filtration.), A6457, A6707, A8082 (completely organic, fatty acid ester type antifoam) and A8582 (Sigma Aldrich) (from about 0.001 wt. % to about 0.005 wt. %), J673A (Struktol an alkoxylated fatty acid ester on a vegetable base), P2000 (Fluka Polypropylene glycol) or SB2121 (Struktol). Other commonly used antifoam agents are insoluble oils, polydimethylsiloxanes and other silicones, certain alcohols, stearates and glycols. Oil based defoamers have an oil carrier. The oil might be mineral oil, vegetable oil, white oil or any other oil that is insoluble in the foaming medium, except silicone oil. An oil based defoamer also contains a wax and/or hydrophobic silica to boost the performance. Typical waxes are ethylene bis stearamide (EBS), paraffin waxes, ester waxes and fatty alcohol waxes. These products might also have surfactants to improve emulsification and spreading in the foaming medium. Water based defoamers are different types of oils and waxes dispersed in a water base. The oils are often white oils or vegetable oils and the waxes are long chain fatty alcohol, fatty acid soaps or esters. These are normally best as deaerators, which means they are best at releasing entrained air. Silicone-based defoamers are polymers with silicon backbones. These might be delivered as an oil or a water based emulsion. The silicone compound consists of an hydrophobic silica dispersed in a silicone oil. Emulsifiers are added to ensure that the silicone spreads fast and well in the foaming medium. The silicone compound might also contain silicone glycols and other modified silicone fluids. EO/PO based defoamers contain polyethylene glycol and polypropylene glycol copolymers. They are delivered as oils, water solutions, or water based emulsions. EO/PO copolymers normally have good dispersing properties and are often well suited when deposit problems are an issue. Alkyl polyacrylates are suitable for use as defoamers in non-aqueous systems where air release is more important than the breakdown of surface foam. These defoamers are often delivered in a solvent carrier like petroleum distillates.

The terms "disposable" and "single use" as used are the customary and ordinary use of these terms such as found in the book "Single-Use Technology in Biopharmaceutical Manufacture", Regine Eibl and Dieter Eibl, A John Wiley & Sons Inc.

Any directional terms, including "top", "bottom", "side", "upper", "lower", "above", "below" etc. refer to the respective directions in the appended drawings.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

DRAWINGS

The accompanying drawings illustrate presently preferred embodiments of the present disclosure, and together with the general description given above and the detailed description given below, serve to explain the principles of the present disclosure. As shown throughout the drawings, like reference numerals designate like or corresponding parts.

FIG. 1 refers to one embodiment in which the exhaust gas exit tube is connected to a section of the bioreactor bag wall.

Figure 2:
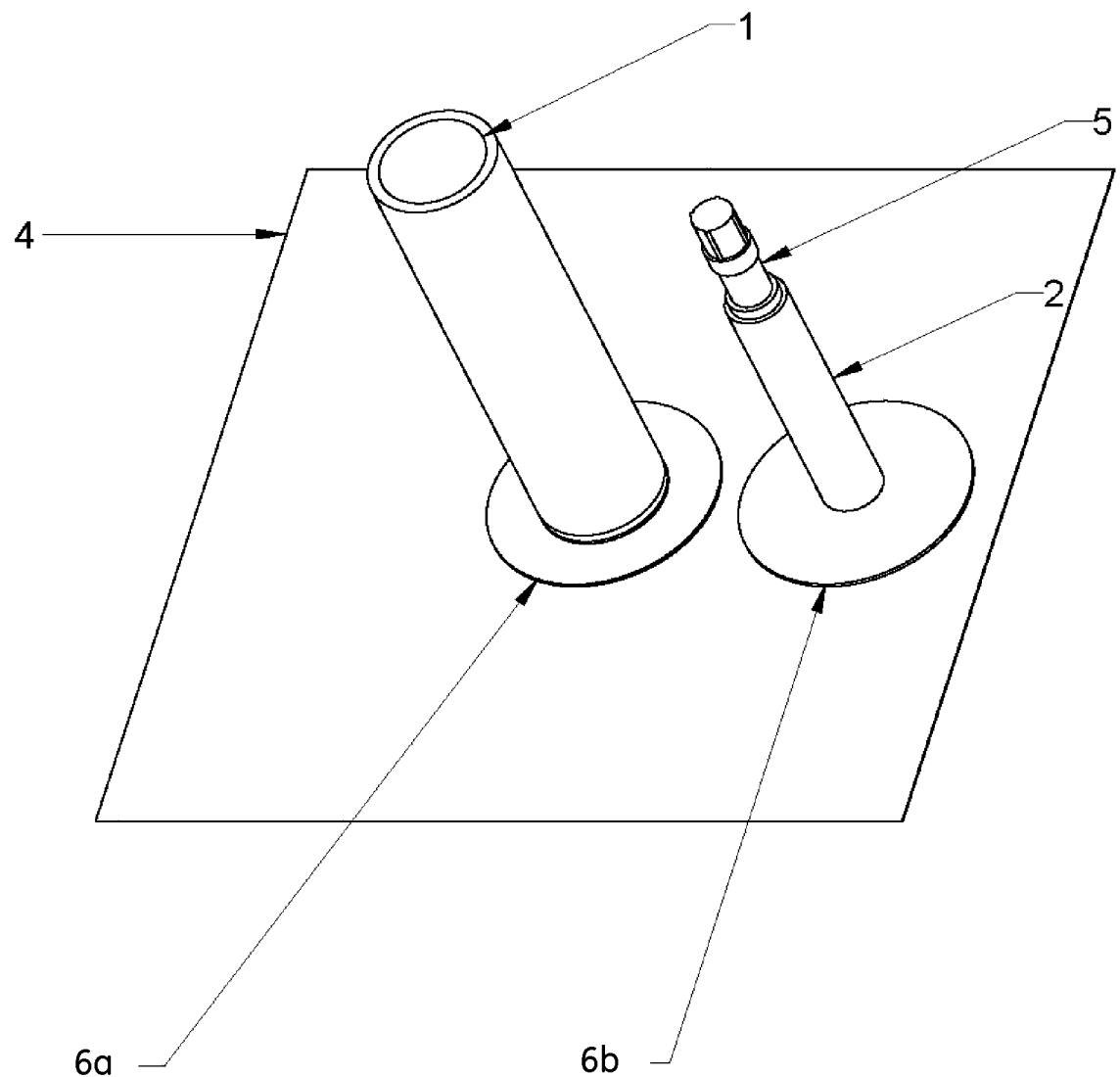

FIG. 2 refers to another embodiment in which the exhaust gas exit tube is connected to a section of the bioreactor bag wall.

Figure 3:
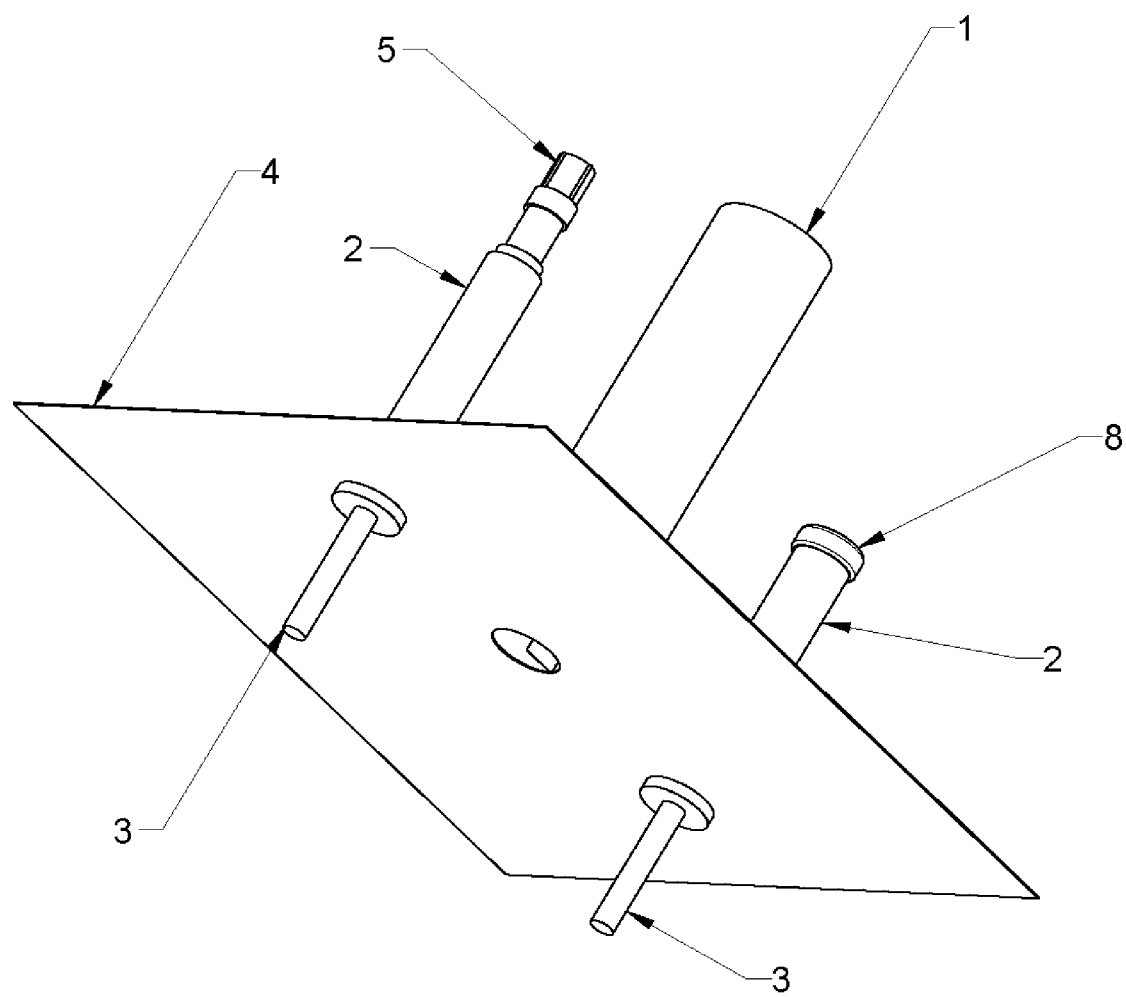

FIG. 3 refers to another embodiment in which the exhaust gas exit tube is connected to a section of the bioreactor bag wall.

Figure 4:
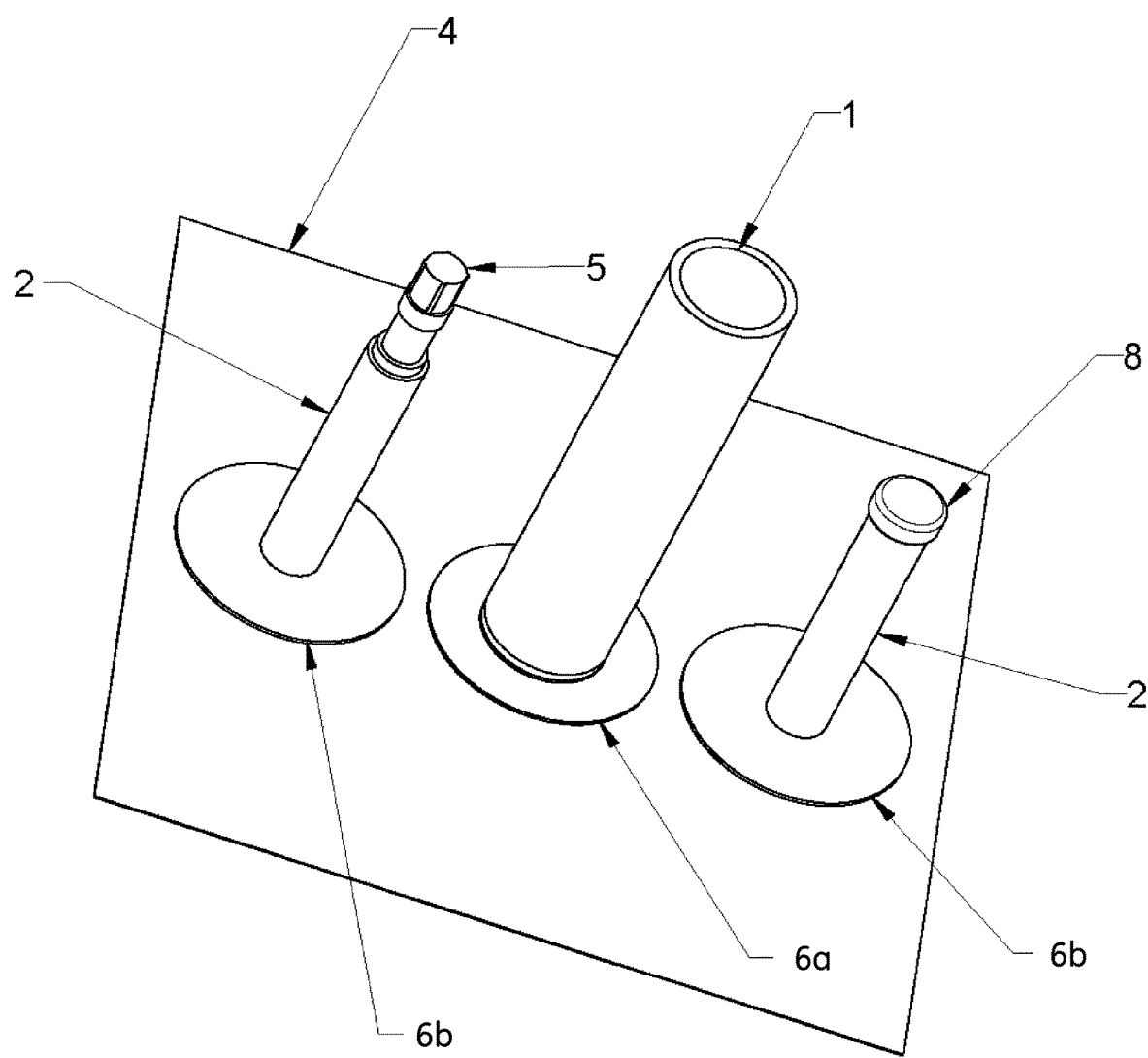

FIG. 4 refers to another embodiment in which the exhaust gas exit tube is connected to a section of the bioreactor bag wall.

Figure 5:
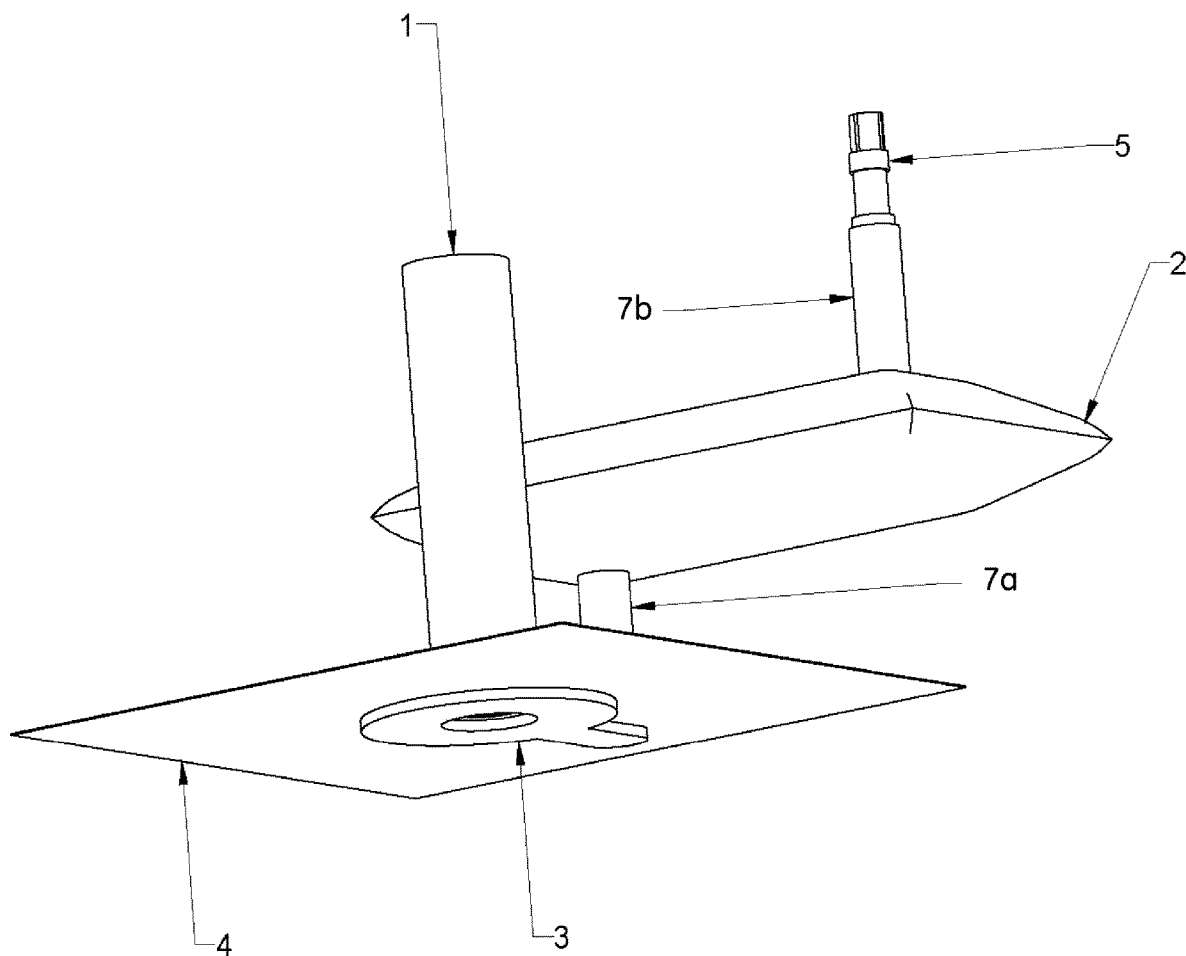

FIG. 5 refers to another embodiment in which the exhaust gas exit tube is connected to a section of the bioreactor bag wall.

Figure 6:
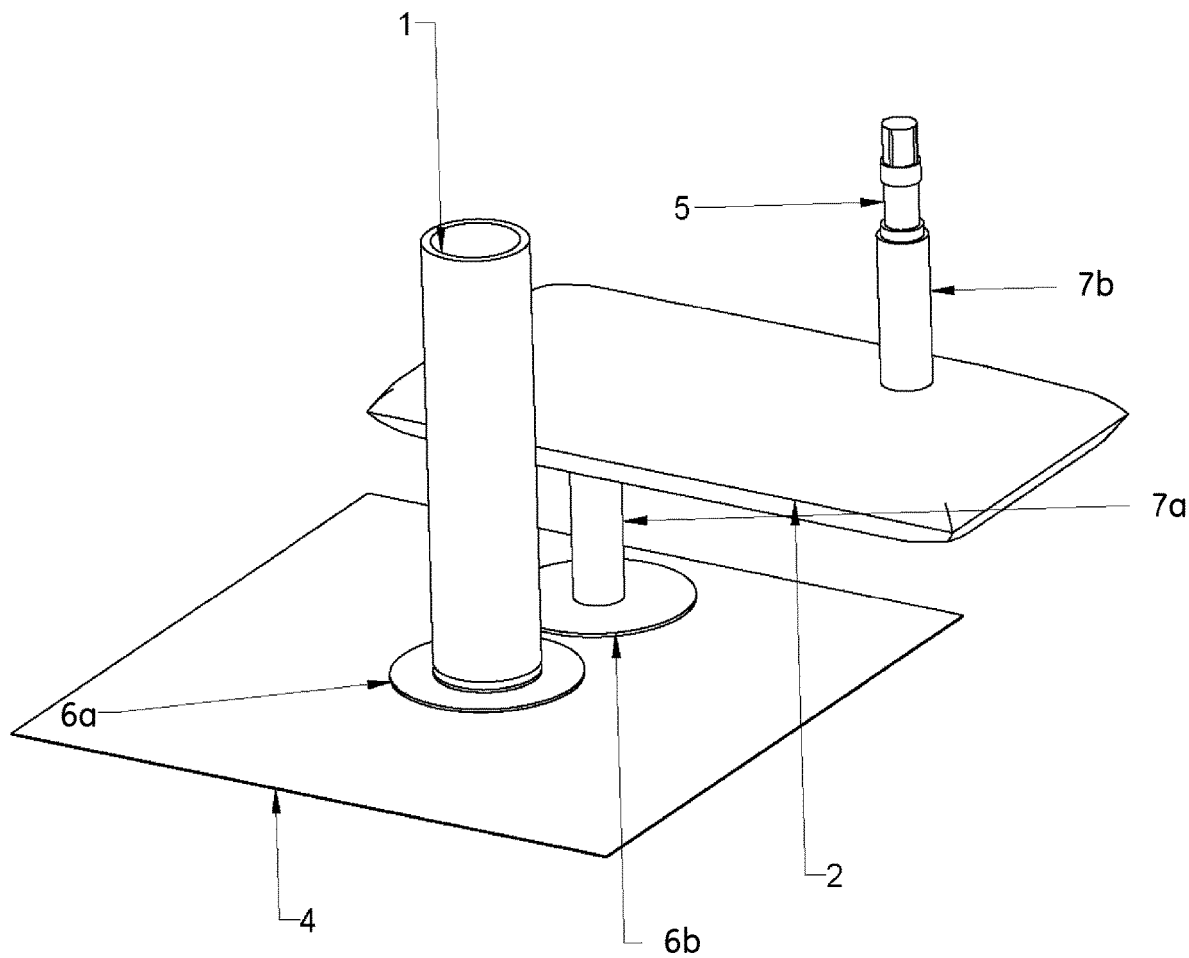

FIG. 6 refers to another embodiment in which the exhaust gas exit tube is connected to a section of the bioreactor bag wall.

Figure 7:
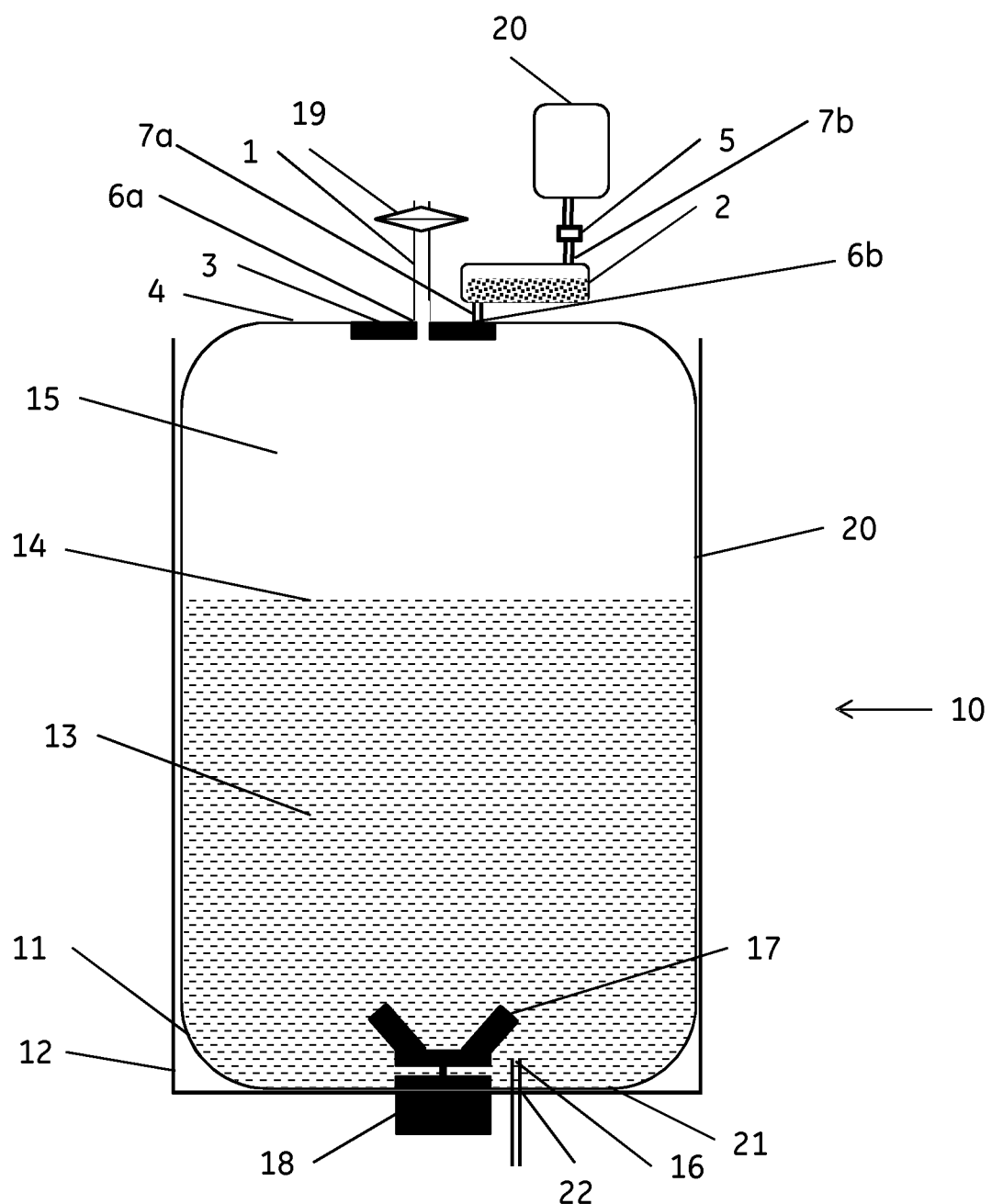

FIG. 7 illustrates a bioreactor apparatus incorporating a passive antifoam apparatus/system, according to another embodiment of the present invention.

DETAILED DESCRIPTION

The present disclosure is generally directed towards the use of antifoam devices and methods so as to improve the use of bioreactor bags. As will be understood, the various diagrams, flow charts and scenarios described herein are only examples, and there are many other scenarios to which the present disclosure will apply.

Referring to FIGS. 1, 2 and 7, two embodiments of the passive antifoam system are illustrated. In these Figures the exhaust gas exit tube 1 is shown connected to a section of the bioreactor bag wall 4 via a port fitment 6a which may be heat welded to the bag film 4. The tube can be made of one of many materials commonly used in the pharmaceutical industry such as platinum cured silicone or C-Flex. The tube can be flexible, semi-rigid or rigid. There can be one or more exhaust gas exit tubes attached to a bioreactor bag 11. The other end of each exhaust tube can be connected to a condenser (not shown), an exhaust filter 19 and/or to another bag (not shown). Inside the bioreactor bag headspace 15 located in proximity to the exhaust gas port fitment is shown the porous or fibrous material pad or wick 3 which retains the antifoam. The porous or fibrous material pad or wick 3 can be formed into many different shapes such as the shape of a disc or ring. The antifoam reservoir in these Figures is depicted as a tubular or cylindrical shaped container 2 which is connected to a section of the bioreactor bag wall 4 (e.g. the top wall) via an antifoam port fitment 6b, which may be heat welded to the bag film 4. An aseptic connector 5 is shown at the top of the antifoam reservoir through which the user can fill the reservoir with antifoam, e.g. from a sterile antifoam container 20 (e.g. a syringe, bag or bottle) attached via the aseptic connector. This aseptic connector 5 could be replaced by a simple plug (not shown) if tube welding a sterile bag of antifoam is to be the method of adding antifoam to the reservoir.

FIG. 3 and FIG. 4 illustrate other embodiments of the passive antifoam system. In these Figures, the exhaust gas exit tube 1 is shown connected to a section of the bioreactor bag wall 4 (e.g. the top wall) via an exhaust gas port fitment 6a which can be heat welded to the bag film 4. The tube can be made of one of many materials commonly used in the pharmaceutical industry such as platinum cured silicone or C-Flex. The tube can be flexible, semi-rigid or rigid. There can be one or more exhaust gas exit tubes attached to a bioreactor bag 11. The other end of the exhaust tube can be connected to a condenser (not shown), an exhaust filter 19 and/or to another bag (not shown). Inside the bioreactor bag headspace 15 located in proximity to the exhaust gas port fitment are one or more porous or fibrous material pads or wicks 3 which retain the antifoam. The porous or fibrous material pads or wicks 3 can be formed into many different shapes such as the shape of a cylinder or tube. The antifoam reservoirs in these Figures are depicted as a tubular or cylindrical shaped container 2 which is connected to a section of the bioreactor bag wall 4 (e.g. the top wall) via an antifoam port fitment 6b heat welded to the bag film 4. An aseptic connector 5 is shown at the top of one of the antifoam reservoirs through which the user can fill the reservoir with antifoam. The aseptic connector 5 could be replaced by a simple tube plug 8 if tube welding a sterile bag of antifoam is to be the method of adding antifoam to the reservoir.

FIG. 5 and FIG. 6 illustrate other embodiments of the passive antifoam system. In these Figures, the exhaust gas exit tube 1 is shown connected to a section of the bioreactor bag wall 4 via an exhaust gas port fitment 6a which can be heat welded to the bag film 4. The tube can be made of one of many materials commonly used in the pharmaceutical industry such as platinum cured silicone or C-Flex. The tube can be flexible, semi-rigid or rigid. There can be one or more exhaust gas exit tubes attached to a bioreactor bag 11. The other end of each exhaust tube can be connected to a condenser (not shown), an exhaust filter 19 or to another bag (not shown). Inside the bioreactor bag headspace 15 located in proximity to the exhaust gas port fitment are one or more porous or fibrous material pads or wicks 3 which retain the antifoam. The porous or fibrous material pads or wicks 3 can be formed into many different shapes such as the shape of a disc or ring. The antifoam reservoir is in this figure shown to be a bag shaped container 2 which is connected through a section of tubing 7a to a section of the bioreactor bag wall 4 via an antifoam port fitment 6b heat welded to the bag film 4. An aseptic connector 5 is shown at the top of a section of tubing 7b through which the user can fill the reservoir with antifoam. The aseptic connector 5 could be replaced by a simple tube plug (not shown) if tube welding a sterile bag of antifoam is to be the method of adding antifoam to the reservoir.

FIG. 7 illustrates a bioreactor apparatus 10, incorporating the passive antifoam apparatus/system as disclosed above. The bioreactor apparatus can e.g. include a rigid support vessel 12, inside which a single-use flexible bioreactor bag 11 is located. The bag can have a top wall 4, a side wall 20 and a bottom wall 21 and may e.g. be of a generally cylindrical shape. It may have a volume of e.g. 5-5000 L, such as 10-5000 L or 10-2000 L. The bioreactor apparatus may comprise an agitator 17, which can e.g. be a magnetically driven agitator 17 inside the bag with a magnetic agitator drive unit 18 outside the bag. When in use, the bag is partially filled with liquid (cell culture) 13 up to a liquid level 14, leaving a headspace 15 in the bag above the liquid level. The bag typically comprises a plurality of port fitments, e.g. 6a,6b,22 etc. for transport of fluids through one or more of the bag walls. The bag may also be equipped with a sparger 16 for sparging the cell culture with a gas such as air or oxygen via a sparger port 22. During use of the bioreactor apparatus, foaming may be induced e.g. by sparging and/or agitation and if the foam fills the headspace it may be entrained in the exhaust gas tube 1 and can e.g. cause blockage of the exhaust filter 19. With the passive antifoam apparatus in place, antifoam is transported from antifoam reservoir 2 into the porous object/pad 3 and when the foam contacts the porous object/pad, antifoam is transferred to the foam lamellae and the foam collapses. The transport of the antifoam can e.g. be by gravity flow from the reservoir 2 to the porous object 3 and further by wicking through the porous object. The reservoir can suitably be placed above the porous object during use and the vertical distance from an antifoam liquid level in the reservoir to the porous object can e.g. be at least 5 mm, such as 5 mm-50 cm or 1-20 cm. The vertical distance may be adjusted to provide a desirable extent of gravity flow and wicking. The volume of the reservoir may e.g. be less than 1% of the bag volume, such as 0.01-1% of the bag volume. Thus, the volume of the reservoir may e.g. be 1 mL-50 L, such as 5 mL-1 L. The amount of antifoam released from the porous object in each instance of foam contact can e.g. be less than 1 mL, such as 1 µL-1 mL or 1 µL-100 µL.

Thus, while there have been shown, described and pointed out, fundamental novel features of the invention as applied to the exemplary embodiments thereof, it will be understood that various omissions and substitutions and changes in the form and details of devices and methods illustrated, and in their operation, may be made by those skilled in the art without departing from the spirit or scope of the invention. Moreover, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A passive automatic antifoam delivery apparatus for use with a single-use bioreactor comprising:
    a porous object secured in the bioreactor proximally to an exhaust gas port and/or in an exhaust gas line fluidically connected to said exhaust gas port,
    wherein said porous object is fluidically connected to an antifoam reservoir and arranged to absorb and/or wick antifoam from said antifoam reservoir and to release antifoam when foam from the bioreactor rises to a level wherein it makes contact with the porous object;
    wherein said apparatus is configured to dispense said antifoam from said reservoir to said porous object without use of a sensor to detect said foam and without active control over said dispensing of said antifoam;
    wherein said porous object is ring-shaped and is positioned so as to surround said exhaust gas port.

2. The passive automatic antifoam delivery apparatus according to claim 1 wherein said antifoam reservoir is external to the bioreactor and connected to the porous object via an antifoam port in a wall of the bioreactor.

3. The passive automatic antifoam delivery apparatus according to claim 2, wherein said antifoam port is located in a top wall of the bioreactor.

4. The passive automatic antifoam delivery apparatus according to claim 1 wherein said porous object is located in a headspace of said bioreactor.

5. The passive automatic antifoam delivery apparatus according to claim 1 wherein said porous object is of medical grade.

6. The passive automatic antifoam delivery apparatus according to claim 1 wherein said porous object is in direct contact with an antifoam reservoir attached to the bag or tubing and the antifoam is introduced into the antifoam reservoir by a user via a sterile syringe fitting or by tube welding of a small container of antifoam.

7. The passive automatic antifoam delivery apparatus according to claim 1 wherein said antifoam is selected from polydimethylsiloxane, block copolymers of polyethylene glycol and polypropylene glycol, polypropylene based polyether dispersions, fatty acid esters, insoluble oils, polydimethylsiloxanes, mineral oil, vegetable oil, and EO/PO based defoamers containing polyethylene glycol and polypropylene glycol copolymers.

8. The passive automatic antifoam delivery apparatus according to claim 1 wherein said porous object comprises open cell porous foams, fibrous mesh or pads or sintered bead foams.

9. The passive automatic antifoam delivery apparatus according to claim 1 wherein said porous object comprises polymeric plastic materials, metals or metal alloys or ceramics.

10. The passive automatic antifoam delivery apparatus according to claim 1 wherein said porous object comprises polymeric plastic materials selected from polyethylene, polypropylene, polyester, polyolefins, polyamides, polyurethane, acrylics, and styrenics.

11. The passive automatic antifoam delivery apparatus according to claim 1 wherein said porous object comprises metals or metal alloys selected from titanium and stainless steel.

12. The passive automatic antifoam delivery apparatus according to claim 1 wherein said porous object comprises ceramics selected from silicon nitride and zirconium dioxide.

13. The passive automatic antifoam delivery apparatus of claim 1 further comprising:
    a bioreactor apparatus.

14. The passive automatic antifoam delivery apparatus of claim 13 wherein the bioreactor apparatus further comprises a single-use flexible bioreactor bag, mounted in a rigid support vessel.

15. The passive automatic antifoam delivery apparatus of claim 13 wherein the bioreactor apparatus further comprises a magnetically driven agitator.

16. The passive automatic antifoam delivery apparatus of claim 13 wherein the bioreactor apparatus further comprises a sparger.

17. The passive automatic antifoam delivery apparatus of claim 13 wherein the bioreactor apparatus further comprises said exhaust gas port and said exhaust gas line.

18. The passive automatic antifoam delivery apparatus of claim 17 wherein the bioreactor apparatus further comprises an exhaust filter, fluidically connected to said exhaust gas line.

19. The passive automatic antifoam delivery apparatus of claim 1, wherein said porous object is a plurality of porous objects, each being fluidically connected to said antifoam reservoir and arranged to absorb and/or wick antifoam from said antifoam reservoir and to release antifoam when foam from the bioreactor rises to a level wherein it makes contact with the porous object.

* * * * *